(12) United States Patent
Kim et al.

(10) Patent No.: US 11,034,993 B2
(45) Date of Patent: Jun. 15, 2021

(54) ASSAY TO MEASURE FACTOR XA INHIBITORS

(71) Applicant: McMaster University, Hamilton (CA)

(72) Inventors: Paul Y. Kim, Mississauga (CA); Chengliang Wu, Binbrook (CA)

(73) Assignee: McMaster University, Hamilton (CA)

( * ) Notice: Subject to any disclaimer, the term of this patent is extended or adjusted under 35 U.S.C. 154(b) by 118 days.

(21) Appl. No.: 16/266,427

(22) Filed: Feb. 4, 2019

(65) Prior Publication Data
US 2019/0241931 A1 Aug. 8, 2019

Related U.S. Application Data

(60) Provisional application No. 62/626,389, filed on Feb. 5, 2018.

(51) Int. Cl.
| | | |
|---|---|---|
| *C12Q 1/56* | (2006.01) | |
| *A61P 7/02* | (2006.01) | |
| *G01N 33/86* | (2006.01) | |
| *G01N 33/68* | (2006.01) | |

(52) U.S. Cl.
CPC ........... *C12Q 1/56* (2013.01); *G01N 33/6893* (2013.01); *G01N 33/86* (2013.01); *G01N 2333/81* (2013.01); *G01N 2333/96444* (2013.01); *G01N 2800/22* (2013.01)

(58) Field of Classification Search
None
See application file for complete search history.

(56) References Cited

PUBLICATIONS

Samama, M. M., Contant, G., Spiro, T. E., Perzborn, E., Guinet, C., Gourmelin, Y., Le Flem, L., Rohde, G., and Martinoli, J. L. (2012), "Evaluation of the anti-factor Xa chromogenic assay for the measurement of rivaroxaban plasma concentrations using calibrators and controls". Thromb. Haemost. 107, 379-387.

Stangier, J., Rathgen, K., Stahle, H., Gansser, D., and Roth, W. (2007), "The pharmacokinetics, pharmacodynamics and tolerability of dabigatran etexilate, a new oral direct thrombin inhibitor, in healthy male subjects". Br. J. Clin. Pharmacol. 64, 292-303.

Brufatto, N. and Nesheim, M. E. (2001), "The use of prothrombin(S525C) labeled with fluorescein to directly study the inhibition of prothrombinase by antithrombin during prothrombin activation". J. Biol. Chem. 276, 17663-17671.

*Primary Examiner* — Karen Cochrane Carlson
(74) *Attorney, Agent, or Firm* — Melanie Szweras; Bereskin & Parr LLP/S.E.N.C.R.L., s.r.l.

(57) ABSTRACT

The present disclosure relates to an assay that measures the level of factor Xa inhibitors in a sample by detecting residual factor Xa activity. In particular, the assay utilizes a mutant variant of prothrombin that lacks proteolytic activity; a prothrombinase complex mixture; and a thrombin-specific inhibitor and measures the factor Xa activity.

19 Claims, 5 Drawing Sheets

Specification includes a Sequence Listing.

SEQUENCE LISTING

<160> NUMBER OF SEQ ID NOS: 1

<210> SEQ ID NO 1
<211> LENGTH: 622
<212> TYPE: PRT

<213> ORGANISM: Homo sapiens

<400> SEQUENCE: 1

```
Met Ala His Val Arg Gly Leu Gln Leu Pro Gly Cys Leu Ala Leu Ala
1               5                  10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Glu Thr Gly Asp Gly Leu Asp
    290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

Asp Ala Glu Ile Gly Met Ser Pro Trp Gln Val Met Leu Phe Arg Lys
    370                 375                 380

Ser Pro Gln Glu Leu Leu Cys Gly Ala Ser Leu Ile Ser Asp Arg Trp
385                 390                 395                 400
```

-continued

```
Val Leu Thr Ala Ala His Cys Leu Leu Tyr Pro Pro Trp Asp Lys Asn
            405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
            485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
            515                 520                 525

Pro Ile Val Glu Arg Pro Val Cys Lys Asp Ser Thr Arg Ile Arg Ile
    530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
            565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
    610                 615                 620
```

ASSAY TO MEASURE FACTOR XA INHIBITORS

CROSS REFERENCE TO RELATED APPLICATIONS

This application claims priority to U.S. Provisional Patent Application No. 62/626,389 filed on Feb. 5, 2018, the content of which is hereby incorporated by reference in its entirety.

INCORPORATION OF SEQUENCE LISTING

A computer readable form of the Sequence Listing "P55419US01_Sequence_Listing_ST25.txt" (5,598 bytes), submitted via EFS-Web and created on Feb. 4, 2019, is herein incorporated by reference.

FIELD

The present application relates to an assay for quantifying levels of factor Xa inhibitors, and in particular, to an assay for measuring residual levels of factor Xa activity in a liquid sample.

BACKGROUND

A new class of anticoagulant drugs often referred to as direct oral anticoagulants (DOAC) are being used more frequently in the treatment and prevention of arterial and venous thrombosis (1). Two main groups of DOACs are classified as targeting either thrombin or factor (F) Xa. Rivaroxaban and apixaban are the most commonly used anti-FXa direct oral anticoagulants (DOAC), with indications for prevention of stroke in non-valvular atrial fibrillation as well as treatment and prevention of venous thromboembolism. As such, with the increased use of anti-FXa DOACs, it is becoming more important to be able to efficiently and accurately measure the levels of these agents in the blood of patients (1-3).

A distinct advantage of these new DOACs is that, unlike warfarin, on-going monitoring of anticoagulation is not as necessary due to their predictable pharmacokinetics and bioavailability; thus they have been adopted despite limited ability to measure their levels. However, in some situations accurate quantitation of anti-FXa DOACs is needed, for instance, when a patient stops anticoagulation in preparation for surgery (1,4). Current guidelines by different organizations offer conflicting recommendations of when patients should stop their anti-FXa DOAC which results in miscommunication that often leads to delayed patient care that wastes time, money, and healthcare resources (5-8).

The main cause of these issues is that currently there are no readily available methods that can accurately measure very low levels of these anti-FXa DOACs (9-11) with relative ease and accuracy. The inability to correlate the levels of anti-FXa DOACs with bleeding risk remains the largest reason for disparate recommendations of fixed time post-cessation of anticoagulation prior to high-bleed risks procedures, including epidural anaesthesia (4,6,7). This is further complicated by renal impairment of patients, resulting in varied clearance of these DOACs (1,5,6). Currently there are two major methods used to accurately quantify low levels of anti-FXa DOAC levels in the blood of patients: a chromogenic substrate enzyme assay (12), and a method that utilizes high-performance liquid chromatography (HPLC) to isolate and quantify DOACs (13). There are two major drawbacks on these methods. The HPLC assay is only done in research facilities, thus not practical for use as a diagnostic tool in a clinical setting. The chromogenic assay needs a skilled technician in a specialty laboratory to perform, while also lacking the sensitivity as the assay cannot accurately detect DOACs less than 20 ng/mL (~45 nM) (2,9,10,14). This becomes a bigger issue when accurate quantitation of anti-FXa DOACs is needed, for instance, when a patient stops anticoagulation in preparation for surgery.

SUMMARY

The present disclosure provides a simple assay that is sensitive to levels of anti-FXa DOACs below the current limit of detection of available assays at specialized coagulation laboratories (20 ng/mL or 45 nM). The ability of this assay to measure DOACs such as rivaroxaban or apixaban in whole blood would make these methods ideal for testing for anticoagulation on an on-going basis to 1) ensure that patients are taking the drugs as recommended to be in therapeutic range, and 2) identify/monitor anticoagulation in patients with altered drug metabolism or clearance (liver or kidney failure, drug-drug interactions or extremes in body weight). This assay as a point-of-care strategy would provide the means for personalized treatment and care during anticoagulation.

Accordingly, herein provided is an assay for determining the level of factor Xa inhibitors in a liquid sample, comprising (a) providing a liquid sample with an anticoagulant; (b) adding to the sample: (i) a mutant variant of prothrombin that lacks proteolytic activity; (ii) a prothrombinase complex mixture; and (iii) a thrombin-specific inhibitor; (c) measuring the initial rate of cleavage of prothrombin; and (d) determining the concentration of the factor Xa inhibitors in the sample as inversely proportional to the rate detected in c).

In an embodiment, the mutant variant of prothrombin comprises a mutation of the latent active site serine to a cysteine (S525C). In another embodiment, the mutant variant of prothrombin further comprises a mutation at position 155 from arginine to alanine or glutamine or any amino acid that results in loss of cleavage at that site by Factor Xa and/or a mutation at position 284 from arginine to alanine or glutamine or any amino acid that results in loss of cleavage at that site by Factor Xa.

In a further embodiment, the mutant variant of prothrombin comprises a mutation at position 525 from serine to cysteine; a mutation at position 155 from arginine to alanine or glutamine; a mutation at position 271 from arginine to alanine or glutamine; and a mutation at position 284 from arginine to alanine or glutamine.

In one embodiment, the mutant variant of prothrombin is labeled with a fluorescence probe. Any fluorescent probe may be used, for example Alexa-488 or 5-iodoacetamido-fluorescein (5-IAF). In one embodiment, the fluorescence probe is 5-IAF. In an embodiment, the mutant prothrombin generates an inactive and fluorescent final product upon cleavage.

In an embodiment, the rate of the cleavage reaction is measured in c) by a change in fluorescence.

In an embodiment, the thrombin-specific inhibitor is hirudin.

In one embodiment, the prothrombinase complex mixture comprises factor Xa, factor Va, phospholipid vesicles and calcium.

In some embodiment, the factor Xa inhibitors are anti-factor Xa direct oral anticoagulants (DOACs). Anti-factor Xa DOACs may be selected from the group consisting of rivaroxaban, apixaban, edoxaban and betrixaban. In one embodiment, the anti-factor Xa DOAC is rivaroxaban or apixaban.

In other embodiments, the factor Xa inhibitor is a low-molecular weight heparin, such as dalteparin.

In an embodiment, the liquid sample comprises plasma or blood. In an embodiment, the liquid sample is from a patient taking DOACs on an ongoing basis. In another embodiment, the liquid sample is from a patient that has ceased taking DOACs. In an embodiment, the patient that has ceased taking DOACs is scheduled for surgery.

In an embodiment, the assay is not sensitive to other coagulation inhibitors, such as corn trypsin inhibitor or vitamin-K antagonists.

In yet another embodiment, the prothrombinase complex mixture concentration can be varied to measure different levels of factor Xa inhibitors in a liquid sample, for example, higher concentrations of prothrombinase complex mixture can measure higher levels of inhibitor and lower concentrations of prothrombinase complex mixture can measure lower levels of inhibitor. Alternatively, for liquid samples suspected of having high levels of factor Xa inhibitors, the liquid sample is first diluted.

In one embodiment, the assay disclosed herein can measure the factor Xa inhibitors at concentrations of less than 20 ng/mL or 45 nM.

Also disclosed herein is a method of testing anticoagulation of a patient comprising subjecting a blood or plasma sample from the patient to the assay disclosed herein to determine the level of the factor Xa inhibitors in the sample. In one embodiment, the method further comprises collecting the blood or plasma sample from the patient. In yet another embodiment, the method is repeated periodically for a patient that is being treated with DOACs on an ongoing basis. In one embodiment, the patient has altered drug metabolism or clearance.

Further disclosed herein is a method of testing for residual anticoagulant upon cessation of anticoagulation in a patient comprising subjecting a blood or plasma sample from the patient to the assay disclosed herein to measure the levels of the factor Xa inhibitors in the sample. In one embodiment, the patient is scheduled for surgery. In an embodiment, the method further comprises collecting the blood or plasma sample from the patient.

The present disclosure also provides a kit to measure levels of factor Xa inhibitors in a liquid sample comprising a) a mutant variant of prothrombin that lacks proteolytic activity, b) a thrombin-specific inhibitor, and c) a prothrombinase complex mixture. The kit may also include instructions for measuring the levels of the factor Xa inhibitors.

In an embodiment, the kit further comprises an anticoagulant or a container having anticoagulant for collecting a sample. In another embodiment, the kit includes DOAC-free plasma samples or standards.

In an embodiment, the mutant variant of prothrombin comprises a mutation of the latent active site serine to a cysteine (S525C). In another embodiment, the mutant variant of prothrombin further comprises a mutation at position 155 from arginine to alanine or glutamine or any amino acid that results in loss of cleavage at that site by Factor Xa and/or a mutation at position 284 from arginine to alanine or glutamine or any amino acid that results in loss of cleavage at that site by Factor Xa. In a particular embodiment, the mutant variant of prothrombin comprises a mutation at position 525 from serine to cysteine; a mutation at position 155 from arginine to alanine or glutamine; a mutation at position 271 from arginine to alanine or glutamine; and a mutation at position 284 from arginine to alanine or glutamine.

In an embodiment, the mutant prothrombin is labeled with a fluorescence probe.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

DETAILED DESCRIPTION

I. Definitions

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having"

and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "factor Xa" or "FXa" as used herein refers to the activated version of factor X. Factor X can be from any source or organism. Examples of factor X include, without limitation, human factor X (NCBI NP_000495 and Gene ID #2159). When activated by proteolytic cleavage, it forms factor Xa, a serine protease that makes up the enzyme component of the prothrombinase complex. Factor Xa may also include variants or intermediates of factor Xa that contain an intact active site that can be targeted for inhibition by factor Xa inhibitors.

The term "DOAC" as used herein refers to direct oral anticoagulants, a general description for a new class of anticoagulant drug, that are direct inhibitors of factor Xa (including, without limitation, rivaroxaban, apixaban, edoxaban, or betrixaban) or thrombin (including, without limitation, dabigatran).

The term "prothrombin" as used herein refers to prothrombin from any source or organism, for example, human prothrombin (see NCBI Gene ID #2147 or preprotein: NP_000497.1 (SEQ ID NO:1 set out below), which includes the propeptide that is 43 amino acids at the start, shown in italics). Positions of prothrombin used herein refer to prothrombin numbering which is known to a person skilled in the art. For SEQ ID NO:1, position 44 corresponds to position 1 of prothrombin numbering, i.e. the propeptide is removed, so that key residues in prothrombin cleavage/function are in alignment with the numbering (e.g. bolded residues: arginine at positions 155, 271, 284, and 320, and serine at position 525 using prothrombin numbering).

(SEQ ID NO: 1)
MAHVRGLQLPGCLALAALCSLVHSQHVFLAPQQARSLLQRVRRANTF

LEEVRKGNLERECVEETCSYEEAFEALESSTATDVFWAKYTACETAR

-continued
TPRDKLAACLEGNCAEGLGTNYRGHVNITRSGIECQLWRSRYPHKPE

INSTTHPGADLQENFCRNPDSSTTGPWCYTTDPTVRRQECSIPVCGQ

DQVTVAMTPRSEGSSVNLSPPLEQCVPDRGQQYQGRLAVTTHGLPCL

AWASAQAKALSKHQDFNSAVQLVENFCRNPDGDEEGVWCYVAGKPGD

FGYCDLNYCEEAVEEETGDGLDEDSDRAIEGRTATSEYQTFFNPRTF

GSGEADCGLRPLFEKKSLEDKTERELLESYIDGRIVEGSDAEIGMSP

WQVMLFRKSPQELLCGASLISDRWVLTAAHCLLYPPWDKNFTENDLL

VRIGKHSRTRYERNIEKISMLEKIYIHPRYNWRENLDRDIALMKLKK

PVAFSDYIHPVCLPDRETAASLLQAGYKGRVTGWGNLKETWTANVGK

GQPSVLQVVNLPIVERPVCKDSTRIRITDNMFCAGYKPDEGKRGDAC

EGDSGGPFVMKSPFNNRWYQMGIVSWGEGCDRDGKYGFYTHVFRLKK

WIQKVIDQFGE

The term "Flu-II" as used herein refers to a fluorescent mutant variant of prothrombin, whereby its active site serine at position 525 (corresponding to position 568 of SEQ ID NO:1 and bolded and underlined above) has been replaced with a cysteine. This free cysteine is then labeled with a fluorescent probe (such as 5-iodoacetamidofluorescein), resulting in a prothrombin derivative with activation cleavage that can be measured by a change in fluorescence as previously described by Brufatto and Nesheim (J. Biol. Chem. 2001; 276: 17663-71).

The term "residual factor Xa activity" as used herein refers to the activity of the remaining factor Xa that is added to the assay. In particular, known amounts of factor Xa are added in the assay disclosed herein and the residual activity is the activity that remains in the presence of the factor Xa inhibitors in the sample.

The term "low-molecular weight heparin" or "LMWH" as used herein refers to low-molecular weight heparin preparations used in anticoagulation therapy (including, without limitation, bemiparin, nadroparin, reviparin, enoxaparin, pamaparin, certoparin, dalteparin, or tinzaparin).

The term "initial rate of cleavage" refers to cleavage during the initial reaction (where the rate is approximately linear) as measured by detectable signal, typically being the first 15-30%, optionally about the first 20% of the reaction.

Unless otherwise indicated, the definitions and embodiments described in this and other sections are intended to be applicable to all embodiments and aspects of the present application herein described for which they are suitable as would be understood by a person skilled in the art.

Assays:

The present inventors developed an assay that utilizes prothrombin mutant (S525C) that is labeled with a fluorescent probe (5-iodoacetamidofluorescein), referred to as Flu-II (15), as the substrate for measuring residual factor Xa activity in liquid samples, such as plasma and blood. The rate of Flu-II cleavage, as measured by fluorescence change, is then inversely proportional to the inhibitor concentration present in the liquid sample. The assay involves addition of Flu-II into liquid samples in the presence of hirudin to inhibit thrombin-feedback reactions, and the reactions are initiated by the addition of the prothrombinase complex mixture (including factor Xa, factor Va, synthetic vesicles and calcium). DOAC is then quantified by monitoring the fluorescence change using a specific activity conversion value that is specific to that lot of the reagent. The assay is carried out over the course of minutes and the simplicity of executing this assay certainly adds to the appeal of this assay becoming a routine test. The only limitation would be the availability of an instrument to measure fluorescence in such a laboratory.

Accordingly, herein provided is an assay for determining the level of factor Xa inhibitors in a liquid sample, comprising (a) providing a liquid sample with an anticoagulant; (b) adding to the sample: (i) a mutant variant of prothrombin that lacks proteolytic activity; (ii) a prothrombinase complex mixture; and (iii) a thrombin-specific inhibitor; (c) measuring the initial rate of cleavage of prothrombin; and (d) determining the concentration of the factor Xa inhibitors in the sample as inversely proportional to the rate detected in c).

Any anticoagulant that does not inactivate the added clotting factors (factor Xa, Va or Flu-II prothrombin) can be used, such as citrate, heparin and acid citrate dextrose. Anticoagulants can be in lyophilized or crystalline forms, but typically are in solution for rapid mixing.

In an embodiment, the mutant variant of prothrombin that lacks proteolytic activity comprises a mutation of the latent active site serine to a cysteine (S525C) of prothrombin.

The use of a prothrombin derivative S525C is advantageous for a number of reasons. First, because the active site serine is mutated to a cysteine, the resulting thrombin does not possess any proteolytic activity which would otherwise result in a positive feedback and propagation of thrombin generation. To further ensure that no endogenous thrombin remains active, a thrombin-specific inhibitor may be added into the assay. Therefore, any prothrombin cleavage observed is as a direct result of FXa that is provided by the assay and not endogenous FXa generated by the blood or plasma.

In another embodiment, the mutant variant of prothrombin further comprises a mutation at position 155 from arginine to alanine or glutamine or any amino acid that results in loss of cleavage at that site by Factor Xa and/or a mutation at position 284 from arginine to alanine or glutamine or any amino acid that results in loss of cleavage at that site by factor Xa. Other than basic amino acid residues, such as arginine or lysine, any amino acid at those positions should render the protein no longer cleavable by factor Xa.

The thrombin-specific inhibitor is added to ensure positive feedback in the coagulation cascade is not generated and includes, without limitation, hirudin, dabigatran, melagatran and phe-pro-arg-chloromethylketone. In an embodiment, the thrombin-specific inhibitor is hirudin.

In a further embodiment, the mutant variant of prothrombin comprises a mutation at position 525 from serine to cysteine; a mutation at position 155 from arginine to alanine or glutamine; a mutation at position 271 from arginine to alanine or glutamine; and a mutation at position 284 from arginine to alanine or glutamine.

The second advantage of S525C prothrombin is labeling of the only free-thiol group on the cysteine with a fluorescent probe such as 5-IAF, so that any fluorescent change observed is simply due to the cleavage of the mutant variant of prothrombin, such as Flu-II, by the remaining exogenous FXa. This simplifies the complicated analyses of the entire coagulation cascade, where the initial rate of mutant variant of prothrombin (e.g. Flu-II) cleavage is simply inversely proportional to DOAC concentrations without needing the resulting thrombin activity to quantify the kinetics of prothrombin activation.

Accordingly, in one embodiment, the mutant variant of prothrombin is labeled with a fluorescence probe. Any fluorescent probe may be used, for example Alexa-488 or 5-iodoacetamidofluorescein (5-IAF). In one embodiment, the fluorescence probe is 5-IAF.

In another embodiment, the mutant variant of prothrombin generates an inactive and fluorescent final product upon cleavage.

In an embodiment, the rate of the cleavage reaction is measured in c) by a change in fluorescence.

The third advantage of using mutant variant of prothrombin such as Flu-II is that the assay no longer becomes dependent on the intrinsic coagulation factor composition of the individuals since the output simply depends on the cleavage of Flu-II by the exogenous FXa that is also provided by the assay reagent. While prothrombin activation can be triggered by a number of different reagents such as tissue factor or polyphosphates (16,17), these pathways are more up-stream of where prothrombin activation would take place and thus become dependent on the individual procoagulant potential to activate FX. Therefore, activating the assay system with purified FXa along with FVa, phospholipid vesicles, such as those composed of 75% PC and 25% PS (PCPS), and calcium to form the prothrombinase complex, makes the assay independent of these individual differences of the up-stream processes needed to generate FXa.

Accordingly, in one embodiment, the prothrombinase complex mixture comprises factor Xa, factor Va, phospholipid vesicles and calcium. Many types of phospholipid vesicles are commonly used in coagulation assays. The ratio of 75% PC and 25% PS is common but other ratios with PC being the bulk may be used. Phosphatidylethanolamine (PE) may also be used to form a PC/PS/PE mixture.

The assay can also be tailored to be specific for low-dose situations (e.g. measuring residual DOAC for surgery prep upon cessation of anticoagulation) or high-dose situations (e.g. on-going measurement to ensure proper dosing). The range of sensitivity to detect the DOACs can be varied by two methods. The first is to dilute the patient liquid samples containing high DOAC levels (i.e. above limit of detection of currently used chromogenic assay of ~20 ng/mL or ~45 nM) using a standard reference DOAC-free plasma so that the residual FXa activity falls within the appropriate range. The second method is to alter the concentration of the prothrombinase/activating solution; with a higher activator concentration for samples from patients undergoing active therapy or a lower activator concentration for measuring residual DOAC levels upon cessation of anticoagulation. This flexibility and versatility of the assay allows for tailoring and customization to meet various clinical needs.

Accordingly, in one embodiment, the liquid sample is first diluted using DOAC-free plasma when the sample is expected to contain high DOAC levels. In another embodiment, the prothrombinase complex mixture concentration is varied to measure different levels of factor Xa inhibitors in a liquid sample, for example, higher concentrations of prothrombinase complex mixture measures higher levels of inhibitor, for example, for testing anticoagulation on an ongoing basis and lower concentrations of prothrombinase complex mixture (e.g. about 0.1 nM factor Xa/prothrombinase) measures lower levels of inhibitor for testing residual anticoagulant upon cessation of anticoagulation.

In one embodiment, the assay disclosed herein can measure the factor Xa inhibitors at concentrations of less than 20 ng/mL or 45 nM.

The assay is not sensitive to the presence of other coagulation inhibitors such as corn trypsin inhibitor (CTI) or vitamin-K antagonists such as warfarin (since all the necessary coagulation factors are provided by the assay with functionally γ-carboxylated GLA domains).

In some embodiments, the factor Xa inhibitors are anti-factor Xa direct oral anticoagulants. Anti-factor Xa direct oral anticoagulants may be selected from the group consisting of rivaroxaban, apixaban, edoxaban and betrixaban. In one embodiment, the anti-factor Xa direct oral anticoagulant is rivaroxaban or apixaban.

In other embodiments, the factor Xa inhibitor is a low-molecular weight heparin, such as dalteparin.

In an embodiment, the liquid sample comprises plasma or blood. In an embodiment, the liquid sample is from a patient taking DOACs on an ongoing basis. In another embodiment, the liquid sample is from a patient that has ceased taking DOACs. In an embodiment, the patient that has ceased taking DOACs is scheduled for surgery.

Methods

Also disclosed herein is a method of testing anticoagulation of a patient comprising subjecting a blood or plasma sample from the patient to the assay disclosed herein to determine the level of the factor Xa inhibitors in the sample. In one embodiment, the method further comprises collecting the blood or plasma sample from the patient into an anticoagulant. Any anticoagulant that does not inactivate the added clotting factors (factor Xa, Va or Flu-II prothrombin) can be used, such as citrate, heparin and acid citrate dextrose. In yet another embodiment, the method is repeated periodically for a patient that is being treated with DOACs on an ongoing basis. In one embodiment, the patient has altered drug metabolism or clearance.

Further disclosed herein is a method of testing for residual anticoagulant upon cessation of anticoagulation in a patient comprising subjecting a blood or plasma sample from the patient to the assay disclosed herein to measure the levels of the factor Xa inhibitors in the sample. In one embodiment, the patient is scheduled for surgery. In another embodiment, the method further comprises collecting the blood or plasma sample from the patient into an anticoagulant such as citrate.

Kits

The present disclosure also provides a kit to measure levels of factor Xa inhibitors in a liquid sample comprising a) a mutant variant of prothrombin that lacks proteolytic activity as disclosed herein, b) a thrombin-specific inhibitor as disclosed herein, and c) a prothrombinase complex mixture as disclosed herein.

In an embodiment, the mutant variant of prothrombin comprises a mutation of the latent active site serine to a cysteine (S525C). In another embodiment, the mutant variant of prothrombin further comprises a mutation at position 155 from arginine to alanine or glutamine or any amino acid that results in loss of cleavage at that site by Factor Xa and/or a mutation at position 284 from arginine to alanine or glutamine or any amino acid that results in loss of cleavage at that site by Factor Xa. In a particular embodiment, the mutant variant of prothrombin comprises a) a mutation at position 525 from serine to cysteine; a mutation at position 155 from arginine to alanine or glutamine; a mutation at position 271 from arginine to alanine or glutamine; and a mutation at position 284 from arginine to alanine or glutamine.

In an embodiment, the mutant prothrombin is labeled with a fluorescence probe.

The kit may also include instructions for use as well as an anticoagulant or a container containing anti-coagulant for collection of a liquid sample. In another embodiment, the kit includes DOAC-free plasma samples or standards.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

EXAMPLES

Materials and Methods

Materials—Human FXa and FVa were purchased from Haematologic Technologies Inc. (Essex Junction, Vt., USA). QuikChange Lightening Site-Directed Mutagenesis Kit was purchased from Agilent Technologies (Santa Clara, Calif., USA). QIAprep® Spin Miniprep Kit and Plasmid Maxi Kit were purchased from Qiagen (Hilden, Germany). Lipofectamine® 3000 Transfection Kit was purchased from Life Technologies-Invitrogen (Carlsbad, Calif., USA). Baby hamster kidney cells and the pNUT vector, used for mammalian expression, were kindly provided by Dr. Ross MacGillivray (University of British Columbia). Methotrexate (Mayne Pharma Inc., Montreal, Quebec Canada) and Vitamin K1 were purchased from Hamilton General Hospital. Q-Sepharose Fast Flow anion-exchange resin and Mono-Q HR 5/5 column were obtained from GE Healthcare (Burlington, Ontario Canada). Gibco® D-MEM/F-12 media, newborn calf serum and Opti-MEM I media, 0.5% Trypsin-EDTA and Antibiotic-Antimycotic solution were purchased from Thermo Fisher Scientific (Carlsbad, Calif., USA). Phosphatidyl-L-serine, phosphatidyl-L-choline, and XAD-2 resin were obtained from Sigma. Matched-Pair Antibody Set for ELISA of Human Prothrombin Antigen, antithrombin, and antithrombin-depleted plasma were purchased from Affinity Biologicals Inc. (Ancaster, ON, Canada). 5-iodoacetamidofluorescein (5-IAF) was purchased from Marker Gene Technologies Inc. (Eugene, Oreg., USA). The recombinant prothrombin with a single mutation of the latent active site serine to a cysteine (S525C) was isolated and labeled with 5IAF (Flu-II) as described by Brufatto and Nesheim (15). Phospholipid vesicles composed of 75% PC and 25% PS (PCPS) were prepared as previously described (18). Bio-Rad Protein Assay reagent was purchased from Bio-Rad (Mississauga, ON, Canada). Corn trypsin inhibitor (CTI) was from Enzyme Research Labs (South Bend, Ind., USA). Rivaroxaban and apixaban were purchased from Suzhou Howsine Biological Technology Company (Suzhou, China). Hirudin was purchased from EMD Chemicals, Inc. (Gibbstown, N.J., USA). Low-molecular weight heparin (dalteparin, Pfizer) was purchased from the Hamilton General Hospital Pharmacy (Hamilton, ON, Canada).

Rate of Flu-II cleavage by residual FXa with increasing levels of DOACs—To determine residual FXa activity upon inhibition by DOACs, Flu-II cleavage was carried out in plasma or whole blood. A mixture (50 µL) containing 0.4 µM Flu-II, 2 µM hirudin, 33 µL of normal human pooled plasma (NHP), and either rivaroxaban or apixaban at varying concentrations (0 to 30 nM) was placed in a clear-bottom 96-well microtiter plate and fluorescence was monitored continuously with a FlexStation 3 (Molecular Devices, Sunnyvale, Calif., USA) fluorescent plate reader at 37° C. at 3-s intervals, with excitation and emission wavelengths at 495 and 540 nm, respectively, with a 530 nm emission cut-off filter. After one minute of equilibration, 50 µL of a mixture containing 0.1 nM FXa, 10 nM FVa, 50 µM PCPS, and 20 mM CaCl$_2$) was added and mixed by instrument trituration. The initial rates of fluorescence change were then measured and plotted with respect to the final DOAC concentration in the reaction mixture, which results in a 1:2 dilution.

To determine if individual variability would affect the assay, the experiment outlined above was repeated using citrated plasma samples isolated from different individuals. Flu-II cleavage by residual FXa was continuously monitored in the presence of DOAC at varying concentrations (0 to 10 nM final).

To determine whether LMWH would affect the assay, the experiment outlined above was repeated using NHP with LMWH added at varying concentrations (0 to 1 unit/mL final) instead of DOACs. Because the inhibition of FXa by LMWH is antithrombin-dependent, the influence of antithrombin in this test was also investigated. Using antithrombin-depleted plasma instead of NHP, human antithrombin was added back at varying concentrations (0 to 3 µM final) in the presence of 1 unit/mL LMWH.

To test whether Flu-II cleavage by residual FXa can be measured in whole blood, citrated blood was collected to be used in the assay. Rivaroxaban or apixaban was added to the whole blood to mimic blood samples collected from patients taking these drugs. A mixture (50 µL) containing 2 µL of whole blood containing varying levels of the DOACs (0 to 100 nM), 0.4 µM Flu-II, and 2 µM hirudin was monitored with FlexStation 3 fluorescent plate reader as described above. Again after one minute of equilibration, 50 µL of a mixture containing 0.1 nM FXa, 10 nM FVa, 50 µM PCPS, and 20 mM CaCl$_2$ was added and mixed by instrument trituration. The initial rates of fluorescence change was then measured and plotted with respect to the final DOAC concentration in the reaction mixture, which results in a 1:50 dilution.

Results

Example 1. Rate of Flu-II Cleavage with Respect to DOAC Concentration

Figure 1A:
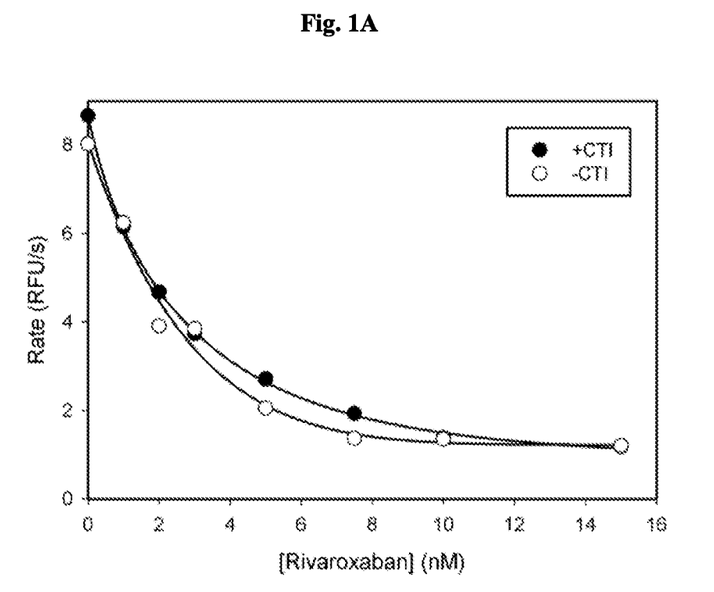
FIG. 1A and FIG. 1B show the residual FXa activity measured by Flu-II cleavage rate as a function of increasing concentration of rivaroxaban (FIG. 1A), or apixaban (FIG. 1B), with (closed) or without (open) corn trypsin inhibitor (CTI).
Figure 1B:
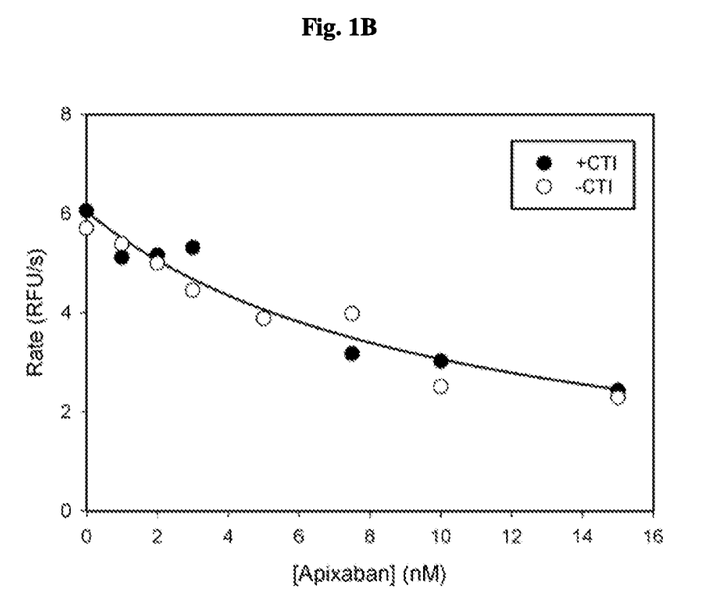

Using NHP as the background, the initial rate of fluorescence change decreased upon increasing levels of DOAC, showing the sensitivity range of the assay for DOAC levels (FIG. 1A and FIG. 1B). Because rivaroxaban is a better inhibitor of factor Xa than apixaban, rivaroxaban showed the greatest sensitivity between 0 and 5 nM (FIG. 1A) with the overall inhibition representing ~85% of total activity. Apixaban showed dose-dependence between 0 and 10 nM (FIG. 1B) with the overall inhibition approaching ~60%. Furthermore, the total change in the rate of Flu-II cleavage is greater with rivaroxaban than apixaban. There was no observable difference by the presence of CTI, which is a commonly used FXIIa inhibitor as the anticoagulant of choice when collecting blood samples (19), regardless of the DOAC used, suggesting that samples of patients that may have been obtained into vacutainers containing CTI is not a concern.

Because the fluorescence change of Flu-II by FXa is reflective of the activation cleavage at Arg320 of prothrombin to generate the intermediate meizothrombin, the substrate could also be a mutant variant of prothrombin that can only generate meizothrombin as the final product (e.g. R271A/Q and/or R155A/Q and/or R284A/Q) to produce similar signal changes. Furthermore, the assay is not necessarily limited to using 5-IAF as the probe to provide a signal change, although the labeling efficiency appears to be better for 5-IAF compared with similar probes such as Alexa-488.

Example 2. Flu-II Cleavage in Individual Plasma Samples

Figure 2:
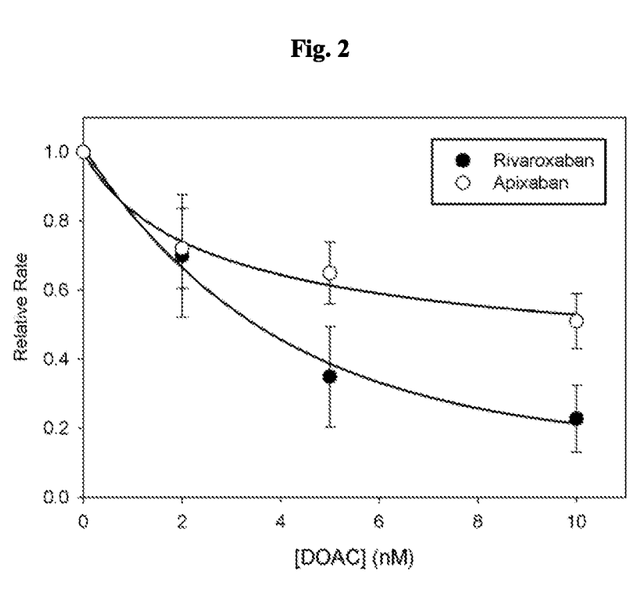
FIG. 2 shows the dose response of the Flu-II cleavage assay to anti-FXa-DOACs in individual plasma samples. Four different individuals were tested with the assay. Either rivaroxaban (closed) or apixaban (open) was added into the isolated plasma samples to a final concentration ranging between 0 and 10 nM. The rates were normalized to no DOACs added. Symbols indicate mean±S.D (n=4).

Similar trends as those with NHP were observed when the reactions were carried out using plasma samples isolated from different individuals (FIG. 2), whereby rivaroxaban showed greater sensitivity compared with apixaban. In addition, rivaroxaban again demonstrated sensitivity between 0 and 5 nM with the maximal inhibition of ~80% of total FXa activity with great reproducibility between individuals. The assay also showed good reproducibility with apixaban concentrations ranging between 0 and 10 nM, with the maximal inhibition approaching ~50%.

The range of sensitivity to detect the DOACs can be varied by two methods. The first is to dilute the patient plasma samples containing high DOAC levels using a standard reference DOAC-free plasma so that the residual FXa activity falls within the appropriate range. The second method is to alter the concentration of the prothrombinase/activating solution; with a higher activator concentration for samples from patients undergoing active therapy or a lower activator concentration for measuring residual DOAC levels upon cessation of anticoagulation. This flexibility and versatility of the assay allows for tailoring and customization to meet various clinical needs.

Figure 3A:
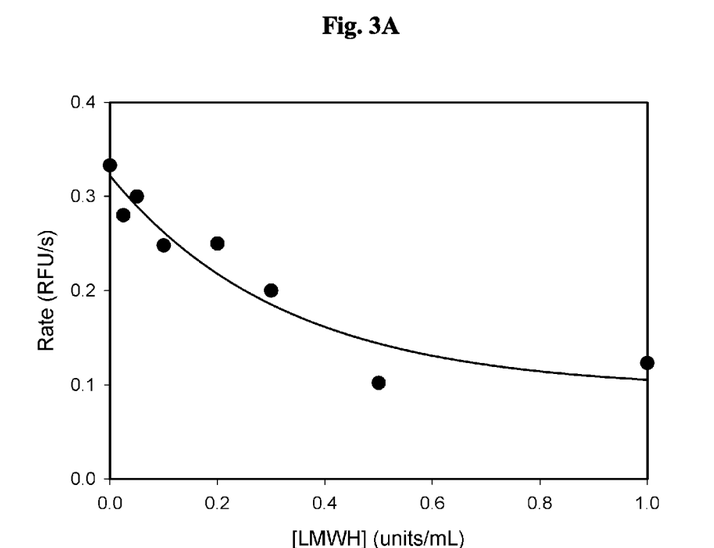
FIG. 3A and FIG. 3B show the effect of low-molecular weight heparin (LMWH) on Flu-II cleavage: Rate of Flu-II cleavage as a response to increasing levels of LMWH in normal human pooled plasma (FIG. 3A). Rate of Flu-II cleavage as a response to increasing levels of antithrombin-III added back to antithrombin-III-depleted plasma in the presence of LMWH (1 unit/mL) (FIG. 3B).
Figure 3B:
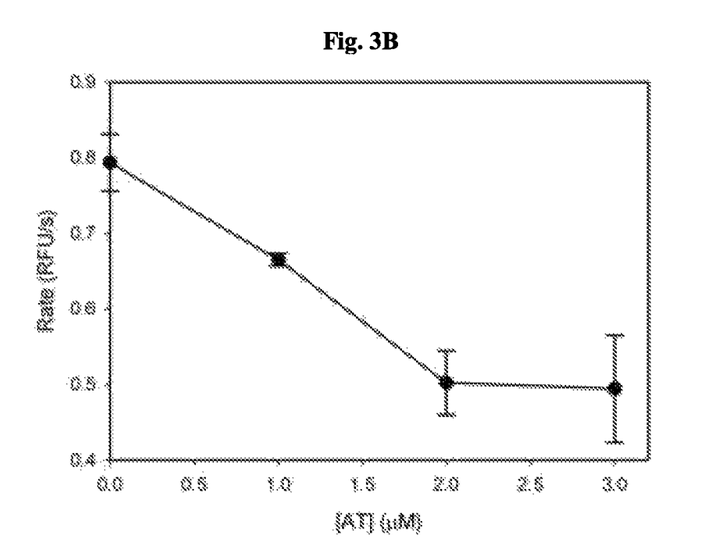

The assay is also sensitive to the levels of LMWH (dalteparin) and antithrombin in the plasma sample (FIG. 3A), whereby dalteparin enhances the inhibitory properties of antithrombin for inhibition of FXa (20). The sensitivity to antithrombin could, however, be ameliorated by supplementing the assay with additional antithrombin, whereby physiologic and higher concentrations (2 µM) of antithrombin does not appear to influence the rate of Flu-II cleavage (FIG. 3B). By doing so, the assay also has the potential to measure low-molecular weight heparin levels in patients.

Example 3. Rate of Flu-II Cleavage in the Whole Blood

Figure 4:
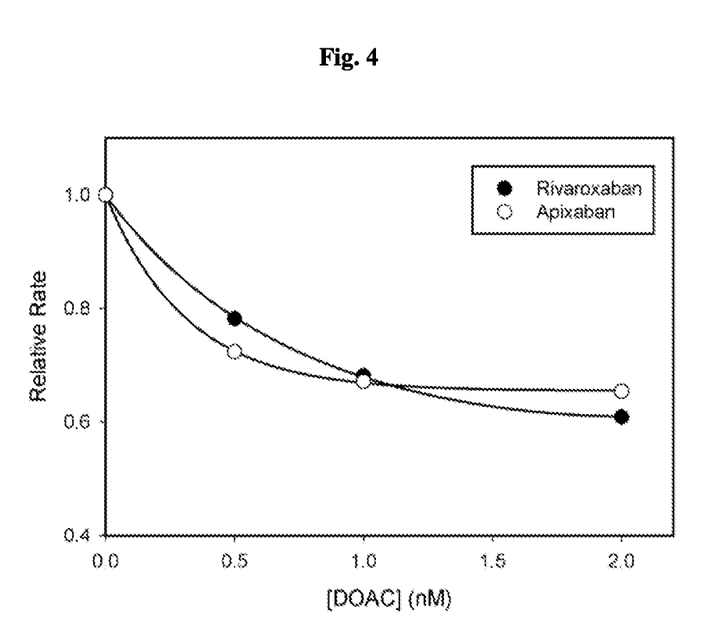
FIG. 4 shows the dose response of the assay to anti-FXa-DOACs in whole blood. Whole blood was collected in citrate to which rivaroxaban (closed) or apixaban (open) was added to achieve an in-blood concentration ranging between 0 and 100 nM.

The initial rate of Flu-II cleavage demonstrated dose-dependence to DOAC concentrations in the whole blood (FIG. 4). Because the reaction results in a 50-fold dilution, the highest dose of the DOAC investigated (2 nM) represents 100 nM circulating in the blood. Unlike with plasma, the dose-response was similar between rivaroxaban and apixaban, with maximal inhibition approaching ~50%. This figure demonstrates the potential of this assay to be implemented as a point-of-care assay for measuring DOACs during treatment.

Figure 5:
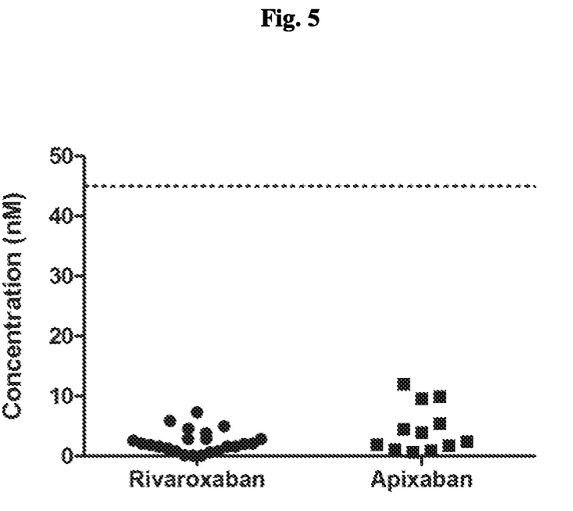
FIG. 5 shows the quantification of the PAUSE study patient plasma samples containing rivaroxaban or apixaban. Samples that were within the linear range of the standard curve without modification or dilution were measured for their respective DOAC levels. Majority of the samples were deemed unmeasurable using the conventional chromogenic assay (closed) while the remainder were measurable with both assays (open). The dotted line represents the detection limit of the conventional chromogenic FXa activity assay.

DOAC levels in plasma samples from patients participating in the Perioperative Anticoagulant Use for Surgery Evaluation (PAUSE) study (24) were measured (FIG. 5). Of the samples tested, 86% of the samples from the rivaroxaban group that were within the linear range of the standard curve were deemed unmeasurable using the conventional chromogenic assay (i.e. <45 nM or 20 ng/mL). For apixaban, however, 55% of the samples that was within the linear range of the standard curve were deemed unmeasurable with the conventional chromogenic assay.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION 1. ten Cate, H. (2013) New oral anticoagulants: discussion on monitoring and adherence should start now! Thromb. J. 11, 8
2. Salmela, B., Joutsi-Korhonen, L., Armstrong, E., and Lassila, R. (2012) Active online assessment of patients using new oral anticoagulants: bleeding risk, compliance, and coagulation analysis. Semin. Thromb. Hemost. 38, 23-30
3. Mismetti, P. and Laporte, S. (2010) New oral antithrombotics: a need for laboratory monitoring. For. J. Thromb. Haemost. 8, 621-626
4. Spyropoulos, A. C. and Douketis, J. D. (2012) How I treat anticoagulated patients undergoing an elective procedure or surgery. Blood 120, 2954-2962
5. Tran, H., Joseph, J., Young, L., McRae, S., Curnow, J., Nandurkar, H., Wood, P., and McLintock, C. (2014) New oral anticoagulants: a practical guide on prescription, laboratory testing and peri-procedural/bleeding management. Australasian Society of Thrombosis and Haemostasis. Intern. Med. J. 44, 525-536
6. Gladstone, D. J., Geerts, W. H., Douketis, J., Ivers, N., Healey, J. S., and Leblanc, K. (2015) How to Monitor Patients Receiving Direct Oral Anticoagulants for Stroke Prevention in Atrial Fibrillation: A Practice Tool Endorsed by Thrombosis Canada, the Canadian Stroke Consortium, the Canadian Cardiovascular Pharmacists Network, and the Canadian Cardiovascular Society. Ann. Intern. Med. 163, 382-385
7. Narouze, S., Benzon, H. T., Provenzano, D. A., Buvanendran, A., De Andres, J., Deer, T. R., Rauck, R., and Huntoon, M. A. (2015) Interventional spine and pain procedures in patients on antiplatelet and anticoagulant medications: guidelines from the American Society of Regional Anesthesia and Pain Medicine, the European Society of Regional Anaesthesia and Pain Therapy, the American Academy of Pain Medicine, the International Neuromodulation Society, the North American Neuromodulation Society, and the World Institute of Pain. Reg Anesth. Pain Med. 40, 182-212
8. Douketis, J. D., Syed, S., and Schulman, S. (2016) Periprocedural Management of Direct Oral Anticoagulants: Comment on the 2015 American Society of Regional Anesthesia and Pain Medicine Guidelines. Reg Anesth. Pain Med. 41, 127-129
9. Samuelson, B. T., Cuker, A., Siegal, D. M., Crowther, M., and Garcia, D. A. (2017) Laboratory Assessment of the Anticoagulant Activity of Direct Oral Anticoagulants: A Systematic Review. Chest 151, 127-138
10. Schlitt, A., Jambor, C., Spannagl, M., Gogarten, W., Schilling, T., and Zwissler, B. (2013) The perioperative management of treatment with anticoagulants and platelet aggregation inhibitors. Dtsch. Arztebl. Int. 110, 525-532
11. Cuker, A., Siegal, D. M., Crowther, M. A., and Garcia, D. A. (2014) Laboratory measurement of the anticoagulant activity of the non-vitamin K oral anticoagulants. J. Am. Coll. Cardiol. 64, 1128-1139
12. Samama, M. M., Contant, G., Spiro, T. E., Perzbom, E., Guinet, C., Gourmelin, Y., Le Flem, L., Rohde, G., and Martinoli, J. L. (2012) Evaluation of the anti-factor Xa chromogenic assay for the measurement of rivaroxaban plasma concentrations using calibrators and controls. Thromb. Haemost. 107, 379-387
13. Stangier, J., Rathgen, K., Stahle, H., Gansser, D., and Roth, W. (2007) The pharmacokinetics, pharmacodynamics and tolerability of dabigatran etexilate, a new oral direct thrombin inhibitor, in healthy male subjects. Br. J. Clin. Pharmacol. 64, 292-303
14. Samama, M. M., Contant, G., Spiro, T. E., Perzbom, E., Le Flem, L., Guinet, C., Gourmelin, Y., Rohde, G., and Martinoli, J. L. (2013) Laboratory assessment of rivaroxaban: a review. Thromb. J. 11, 11
15. Brufatto, N. and Nesheim, M. E. (2001) The use of prothrombin (S525C) labeled with fluorescein to directly study the inhibition of prothrombinase by antithrombin during prothrombin activation. J. Biol. Chem. 276, 17663-17671
16. Gajsiewicz, J. M. and Morrissey, J. H. (2015) Structure-Function Relationship of the Interaction between Tissue Factor and Factor VIIa. Semin. Thromb. Hemost. 41, 682-690
17. Smith, S. A., Mutch, N. J., Baskar, D., Rohloff, P., Docampo, R., and Morrissey, J. H. (2006) Polyphosphate modulates blood coagulation and fibrinolysis. Proc. Natl. Acad. Sci. U. S. A 103, 903-908
18. Bloom, J. W., Nesheim, M. E., and Mann, K. G. (1979) Phospholipid-binding properties of bovine factor V and factor Va. Biochemistry 18, 4419-4425
19. Swartz, M. J., Mitchell, H. L., Cox, D. J., and Reeck, G. R. (1977) Isolation and characterization of trypsin inhibitor from opaque-2 corn seeds. J. Biol. Chem. 252, 81058107
20. Hirsh, J., Anand, S. S., Halperin, J. L., and Fuster, V. (2001) Mechanism of action and pharmacology of unfractionated heparin. Arterioscler. Throm. Vasc. Biol. 21, 1094-1096
21. Douketis, J. D., Spyropoulos, A. C., Anderson, J. M., Arnold, D. M., Bates, S. M., Blostein, M., Carrier, M., Caprini, J. A., Clark, N. P., Coppens, M., Dentali, F., Duncan, J., Gross, P. L., Kassis, J., Kowalski, S., Lee, A. Y., Le Gal, G., Le Templier, G., Li, N., MacKay, E. et al. (2017) The Perioperative Anticoagulant Use for Surgery Evaluation (PAUSE) study for patients on a direct oral anticoagulant who need an elective surgery or procedure: design and rationale. Thromb. Haemost. 117, 2415-2424

The invention claimed is:

1. An assay for determining the concentration of factor Xa inhibitors in a blood or plasma sample from a patient who is taking or has previously taken a factor Xa inhibitor, comprising:
   a) providing a blood or plasma sample collected into an anticoagulant;
   b) adding to the sample:
      i) a fluorescently-labeled mutant variant of prothrombin that lacks proteolytic activity;
      ii) a prothrombinase complex mixture; and
      iii) a thrombin-specific inhibitor;
   c) measuring the initial rate of fluorescently-labeled mutant variant of prothrombin cleavage, wherein the initial rate refers to the first 20% of the reaction indicated by the total fluorescence signal increase divided by the time lapsed; and
   d) determining the concentration of the factor Xa inhibitors in the sample as inversely proportional to the rate detected in c).

2. The assay of claim 1, wherein the mutant variant of prothrombin comprises a mutation of the latent active site serine at position 525 (corresponding to position 568 as shown in SEQ ID NO:1) to cysteine (S525C) and optionally, further comprises a mutation at position 155 (corresponding to position 198 as shown in SEQ ID NO:1) from arginine to alanine or glutamine or any amino acid that results in loss of cleavage at that site by Factor Xa and/or a mutation at position 284 (corresponding to position 327 as shown in SEQ ID NO:1) from arginine to alanine or glutamine or any amino acid that results in loss of cleavage at that site by Factor Xa.

3. The assay of claim 1, wherein the mutant variant of prothrombin comprises:
   a) a mutation at position 525 (corresponding to position 568 as shown in SEQ ID NO:1) from serine to cysteine;
   b) a mutation at position 155 (corresponding to position 198 as shown in SEQ ID NO:1) from arginine to alanine or glutamine;
   c) a mutation at position 271 (corresponding to position 314 as shown in SEQ ID NO:1) from arginine to alanine or glutamine; and
   d) a mutation at position 284 (corresponding to position 327 as shown in SEQ ID NO:1) from arginine to alanine or glutamine.

4. The assay according to claim 1, wherein the fluorescence probe is 5-iodoacetamidofluorescein.

5. The assay of claim 1, wherein the thrombin-specific inhibitor is hirudin.

6. The assay of claim 1, wherein the prothrombinase complex mixture comprises factor Xa, factor Va, phospholipid vesicles and calcium.

7. The assay of claim 1, wherein the factor Xa inhibitors are anti-factor Xa direct oral anticoagulants or low-molecular weight heparin.

8. The assay according to claim 7, wherein the anti-factor Xa direct oral anticoagulants are selected from the group consisting of rivaroxaban, apixaban, edoxaban and betrixaban.

9. The assay according to claim 8, wherein the anti-factor Xa direct oral anticoagulant is rivaroxaban or apixaban.

10. The assay according to claim 7, wherein the low-molecular weight heparin is dalteparin.

11. The assay according to claim 1, wherein the plasma or blood sample is first diluted.

12. The assay according to claim 1, wherein the factor Xa inhibitors can be measured at concentrations of less than 20 ng/mL or 45 nM.

13. A method of testing anticoagulation of a patient comprising periodically collecting a blood or plasma sample from the patient and subjecting the sample to the assay of claim 1 to measure the concentration of the factor Xa inhibitors.

14. A method of testing for residual anticoagulant upon cessation of anticoagulation of a patient comprising collecting a blood or plasma sample from the patient and subjecting the sample to the assay of claim 1 to measure the concentration of the factor Xa inhibitors.

15. The method of claim 14, wherein the patient is scheduled for surgery.

16. A kit to measure concentration of factor Xa inhibitors in a liquid sample comprising:

a) a mutant variant of prothrombin that lacks proteolytic activity,
b) a thrombin-specific inhibitor,
c) a prothrombinase complex mixture; and
d) instructions for use.

17. The kit of claim 16, wherein the mutant variant of prothrombin comprises a mutation of the latent active site serine to cysteine (S525C; corresponding to position S568C as shown in SEQ ID NO:1) and optionally, further comprises a mutation at position 155 from arginine to alanine or glutamine or any amino acid that results in loss of cleavage at that site by Factor Xa and/or a mutation at position 284 (corresponding to position 327 in SEQ ID NO:1) from arginine to alanine or glutamine or any amino acid that results in loss of cleavage at that site by Factor Xa.

18. The kit of claim 16, wherein the mutant prothrombin is labeled with a fluorescence probe.

19. The kit of claim 16, further comprising an anticoagulant or a container having anticoagulant for collection of a sample.

* * * * *